US012685702B2

(12) United States Patent　(10) Patent No.:　US 12,685,702 B2
Maparu et al.　(45) Date of Patent:　Jul. 21, 2026

(54) SUNSCREEN COMPOSITION CONTAINING BIODEGRADABLE ANTIMICROBIAL POLYMER NANOPARTICLES AS ULTRAVIOLET FILTER

(71) Applicant: Tata Consultancy Services Limited, Mumbai (IN)

(72) Inventors: Auhin Kumar Maparu, Pune (IN); Ashish Masarkar, Pune (IN); Beena Rai, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 846 days.

(21) Appl. No.: 18/087,891

(22) Filed: Dec. 23, 2022

(65) Prior Publication Data

US 2024/0000692 A1　　Jan. 4, 2024

(51) Int. Cl.
　*A61K 8/73*　　　(2006.01)
　*A61Q 17/04*　　(2006.01)
　*B82Y 30/00*　　(2011.01)
(52) U.S. Cl.
　CPC .............. *A61K 8/736* (2013.01); *A61Q 17/04* (2013.01); *A61K 2800/413* (2013.01); *B82Y 30/00* (2013.01)
(58) Field of Classification Search
　None
　See application file for complete search history.

(56) References Cited

FOREIGN PATENT DOCUMENTS

| CN | 112353699 A | 2/2021 | |
| KR | 10-2331844 | 11/2021 | |
| WO | WO-0047177 A1 * | 8/2000 | .............. B82Y 5/00 |

OTHER PUBLICATIONS

Casadidio et al., "Chitin and Chitosans: Characteristics, Eco-Friendly Processes, and Applications in Cosmetic Science," Mar. Drugs, 17(369) (2019).
He hailun et al., "Natural components in sunscreens: Topical formulations with sun protection factor (SPF)," Biomedicine & Pharmacotherapy, 134 (2021).

* cited by examiner

*Primary Examiner* — Nannette Holloman
(74) *Attorney, Agent, or Firm* — Finnegan, Henderson, Farabow, Garrett & Dunner, LLP

(57)　　　　　ABSTRACT

Nanomaterials are an important class of materials for sunscreens. Conventional metal oxide nanoparticles are toxic in nature and leave white patches on skin after application. This disclosure provides a sunscreen composition containing biodegradable antimicrobial polymer nanoparticles as UV filter. The sunscreen composition comprising chitosan nanoparticles, at least one flavoring agent, at least one coloring agent, at least one stabilizer, and at least one preservative, in a defined form, wherein size of the chitosan nanoparticles is ranging from 200 to 900 nm. The size of the chitosan nanoparticles ranging from 200 to 400 nm for air medium, 500 to 700 nm for water medium and 700 to 900 nm for ethanol medium. The chitosan polymer is derived from chitin, a glucosamine polymer. The sunscreen composition is available in the defined form selected from a group consisting of a skin cream, a skin lotion, a powder, a gel, and a sprayable liquid.

13 Claims, 7 Drawing Sheets

SUNSCREEN COMPOSITION CONTAINING BIODEGRADABLE ANTIMICROBIAL POLYMER NANOPARTICLES AS ULTRAVIOLET FILTER

PRIORITY CLAIM

This U.S. patent application claims priority under 35 U.S.C. § 119 to: Indian Patent Application No. 202221029965, filed on May 25, 2022. The entire contents of the aforementioned application are incorporated herein by reference.

TECHNICAL FIELD

The disclosure herein generally relates to the field of cosmetics, and, more particularly, to a sunscreen composition containing biodegradable antimicrobial polymer nanoparticles as ultraviolet (UV) filter.

BACKGROUND

Nanomaterials have emerged as an important class of materials for sunscreen applications in recent times. Unlike chemical sunscreens which protect human skin via absorption of UV light, nanomaterials are acting as physical sunscreen. The physical sunscreens like metal oxide nanoparticles attenuate UV irradiation by absorption and scattering from the skin surface itself and offer lesser penetration/interaction with the deeper layers of skin. For example, titania ($TiO_2$) and zinc oxide (ZnO) nanoparticles are commonly used as UV filter in commercial physical sunscreens.

Conventional metal oxide nanoparticles (e.g. $TiO_2$/ZnO) are opaque in nature due to the high refractive index values of $TiO_2$/ZnO and exhibit white patchy appearance on skin. The size of the said nanoparticles can be reduced to a certain range to overcome the above problem. For example, if the size of the said nanoparticles is reduced to 20-150 nm, whitening effect can be eliminated. However, the resulting ultrafine nanoparticles can penetrate through the skin layers and cause damage to the skin cells. Owing to high surface to volume ratio and photocatalytic nature, these metal oxide nanoparticles induce excessive oxidative stress via formation of reactive oxygen species (ROS) leading to DNA damage and accelerated aging of skin. Further, if they reach the bloodstream, these non-degradable nanoparticles may get circulated throughout the body and accumulate in various organs such as liver, kidney, spleen, heart, brain etc. resulting toxic side effects.

SUMMARY

Embodiments of the present disclosure present technological improvements as solutions to one or more of the above-mentioned technical problems recognized by the inventors in the conventional sunscreen compositions.

In an aspect, a sunscreen composition containing biodegradable antimicrobial polymer nanoparticles as UV filter is provided. The sunscreen composition comprises chitosan nanoparticles as UV filter, at least one flavoring agent, at least one coloring agent, at least one stabilizer, and at least one preservative, wherein the sunscreen composition is present in a defined form and size of the chitosan nanoparticles ranging from 200 to 900 nm. In an embodiment, the size of the chitosan nanoparticles ranging from 200 to 400 nm for air medium, 500 to 700 nm for water medium and 700 to 900 nm for ethanol medium. In an embodiment, the chitosan nanoparticles comprise one of, a) a chitosan polymer and b) derivatives of chitosan polymer. In an embodiment, the chitosan polymer is derived from chitin, wherein chitin is a glucosamine polymer. In an embodiment, the chitosan polymer is non-toxic, biodegradable, and biocompatible. In an embodiment, the chitosan polymer is a cationic polymer. In an embodiment, the chitosan nanoparticles provide antimicrobial protection of human skin from harmful pathogens owing to the antimicrobial property of chitosan polymer. In an embodiment, the chitosan nanoparticles can adhere well on human skin owing to the cationic nature of chitosan polymer. In an embodiment, the chitosan nanoparticles provide attenuation from ultraviolet (UV) radiation in a wavelength range of 290-400 nm. In an embodiment, the chitosan nanoparticles have an extinction co-efficient in the range of 40-100 $Lgm^{-1}cm^{-1}$ in air medium under UV radiation in the wavelength range of 290-400 nm. In an embodiment. the chitosan nanoparticles have an extinction co-efficient in the range of 10-40 $Lgm^{-1}cm^{-1}$ in water medium under UV radiation in the wavelength range of 290-400 nm. In an embodiment, the chitosan nanoparticles have an extinction co-efficient in the range of 10-30 $Lgm^{-1}cm^{-1}$ in ethanol medium under UV radiation in the wavelength range of 290-400 nm. In an embodiment, the defined form is selected from a group consisting of a skin cream, a skin lotion, a powder, a gel, and a sprayable liquid. In an embodiment, the sunscreen composition is capable of protecting skin from harmful UV radiation.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1A:
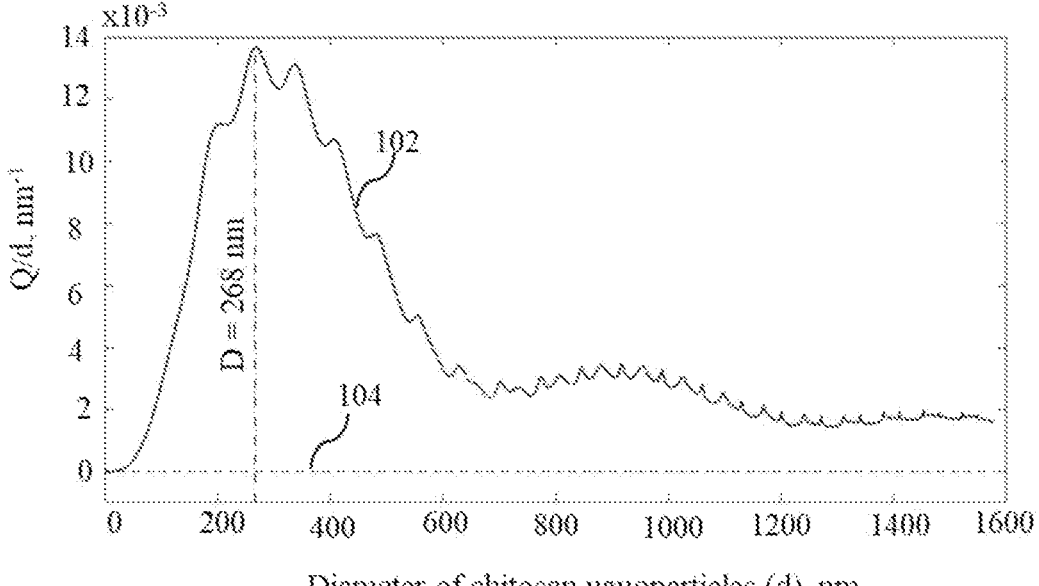
FIGS. 1A, 1B and 1C are graphs showing a relative extinction efficiency ($Q_{ext}$/d), a relative scattering efficiency ($Q_{sca}$/d), and a relative absorption efficiency ($Q_{abs}$/d) of the chitosan nanoparticles in air medium, water medium and ethanol medium respectively, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Conventional physical sunscreens having inorganic ultraviolet (UV) filters such as titania ($TiO_2$), zinc oxide (ZnO) are toxic in nature and leave white patches on skin after application. The present disclosure proposes the usage of chitosan nanoparticles as an alternative to conventional UV filters. Chitosan is a naturally available biopolymer with excellent biocompatibility and biodegradability. Further, it possesses antimicrobial, and skin adherent properties desired for topical applications.

Ultraviolet (UV) radiation is a part of the solar spectrum with wavelengths ranging from 100 to 400 nm. A large part of the most damaging section of the ultraviolet radiation (UVC: 100-290 nm) is absorbed by the ozone layer in the atmosphere. However, a fraction of the radiation (UVB: 290-320 nm and UVA: 320-400 nm) penetrates the atmosphere and affects the skin of humans exposed to the sunlight. UVB radiation may cause redness of skin, sunburns, and increases the risk of basal cell and squamous cell carcinoma due to damage to the DNA of skin cells. UVA radiation may cause sun tanning, photoaging of the skin, and malignant melanoma due to indirect DNA damage by the generation of reactive free radicals. To prevent these problems, improved UV protection can be achieved through the use of UV attenuating materials such as physical and chemical sunscreens.

Chemical sunscreens are generally organic compounds that attenuate UV purely by absorption at the molecular level. On the other hand, physical sunscreens attenuate UV by mechanisms including scattering and reflection as well as absorption.

Further, chemical sunscreens are usually organic compounds which penetrate into the skin to varying extents. Studies indicate that most of the known chemical sunscreens made of the organic compounds have potentially toxic effects on skin cells. Prevalent physical sunscreens afford UV protection by means of a combination of scattering and absorption effects. They are usually metal oxides such as $TiO_2$ and ZnO. Such compounds act as band-gap absorbers, absorbing UV photons due to the gap between the valence and conduction bands similar to semi-conductors. Such physical sunscreen materials, being naturally opaque, are undesirable as they leave white patches on the skin upon application at significant concentrations. A common strategy to overcome this problem is to reduce the size of the physical sunscreen material (particles) to the nano-range. However, the resulting metal oxide nanoparticles may easily penetrate through the skin and have high photocatalytic activity, releasing reactive oxygen species (ROSs) into the skin causing cell damage, accelerating skin aging, and potential carcinogenic effects. Further, the resulting metal oxide nanoparticles may not have natural adherent properties to the skin hence they are liable to be washed off easily and not effective over a long period of time.

Chitosan nanoparticles can be a potential alternative to the existing commercial sunscreen nanoparticles, resolving many of the above health issues without compromising the UV extinction requirement for sunscreen applications. Chitosan is derived from chitin, a glucosamine polymer and possess close similarity with human skin extracellular matrix. Hence, chitosan nanoparticles are non-toxic, biocompatible and biodegradable. Since chitosan is a natural cationic polymer, chitosan nanoparticles adhere well on the skin surface via electrostatic interaction with negatively charged stratum corneum of skin. An additional beneficial feature of chitosan nanoparticles is their antimicrobial activity against the pathogens present on human skin.

Chitosan nanoparticles have been explored for encapsulation and delivery of sunscreen agents in the past. Further, it has been utilized for improving the biocompatibility and decreasing the photocatalytic activity of commercial sunscreen nanoparticles. However, chitosan nanoparticles have not been explored as a standalone UV filter in sunscreen formulation due to the poor UV absorption behavior of chitosan. In the present disclosure, it has been demonstrated that the size of chitosan nanoparticles can be adjusted to obtain maximum scattering of UV irradiation in a particular medium. The extinction coefficient and sun protection factor (SPF) values of the standardized chitosan nanoparticles are significantly higher as compared to the existing commercial metal oxide sunscreen nanoparticles.

In an embodiment, the sunscreen composition of the present disclosure includes chitosan nanoparticles as UV filter, at least one flavoring agent, at least one coloring agent, at least one stabilizer, and at least one preservative. The sunscreen composition is present in a defined form and size of the chitosan nanoparticles ranging from 200 to 900 nm.

In an embodiment, the size of the chitosan nanoparticles ranging from 200 to 400 nm for air medium, 500 to 700 nm for water medium and 700 to 900 nm for ethanol medium is used in the sunscreen composition.

In an embodiment, the chitosan nanoparticles are used in the sunscreen composition. In another embodiment, chitosan nanoparticles comprising one or more derivatives of chitosan polymer are used in the sunscreen composition. In an embodiment, the chitosan polymer is derived from chitin, a glucosamine polymer. The chitosan polymer is a cationic polymer.

In an embodiment, the chitosan polymer is non-toxic, biodegradable and biocompatible. The chitosan nanoparticles provide antimicrobial protection of human skin from harmful pathogens owing to the antimicrobial property of chitosan polymer. The chitosan nanoparticles can adhere well on human skin owing to the cationic nature of chitosan polymer.

In an embodiment, the chitosan nanoparticles provide attenuation from UV radiation in a wavelength range of 290-400 nm. The chitosan nanoparticles have an extinction co-efficient in the range of 40-100 $Lgm^{-1}cm^{-1}$ in air medium under UV radiation in the wavelength range of 290-400 nm.

In an embodiment, the chitosan nanoparticles provide an extinction co-efficient in the range of 10-40 $Lgm^{-1}cm^{-1}$ in water medium under UV radiation in the wavelength range of 290-400 nm.

In an embodiment, the chitosan nanoparticles provide an extinction co-efficient in the range of 10-30 $Lgm^{-1}cm^{-1}$ in ethanol medium under UV radiation in the wavelength range of 290-400 nm.

The defined form is selected from a group consisting of a skin cream, a skin lotion, a powder, a gel, and a sprayable liquid. Here, the term "defined form" refers to the state of formulation.

In accordance with the embodiments of the present disclosure, at least one flavoring agent is included in the sunscreen composition to get a flavoring effect. In an embodiment, at least one flavoring agent is selected from mints such as peppermint and menthol, cirrus flavors such as orange and lemon, vanilla, cinnamon, various other fruit flavors such as apple, mango, pineapple, and so on, both individual and mixed.

In accordance with the embodiments of the present disclosure, at least one coloring agent is included in the sunscreen composition. In an embodiment, at least one coloring agent is selected from pigments or dyes, or a combination thereof. In accordance with the embodiments of the present disclosure, at least one stabilizer is included in the sunscreen composition. In an embodiment, at least one stabilizer is selected from surfactants, emulsifiers, dispersants, detergents, or a combination thereof. Further, in accordance with the embodiments of the present disclosure, at least one preservative is included in the sunscreen composition. In an embodiment, at least one preservative is selected from antioxidants, vitamins, their derivatives, or a combination thereof.

In accordance with the embodiments of the present disclosure, the UV attenuation ability of the chitosan nanoparticle is obtained using Mie theory as explained below. The total absorbance A (due to absorption and scattering) of a solution containing particles of radius r, number density N and path length 1 can be expressed in terms of extinction efficiency $Q_{ext}$ as given in equation (1), $$A = \frac{\pi r^2 Q_{ext} l N}{2.303} \tag{1}$$

The number density N can be expressed as given in equation (2), $$N = c/(\rho V) \tag{2}$$

where, $\rho$ is the density, c is the concentration and V is the volume of particles. Assuming the particles to be spherical, we can write, $V=(4/3)\pi r^3$. Hence A can be rewritten as given in equation (3)

$$A = \frac{Q_{ext} l c}{1.535 \rho d} \tag{3}$$

where, d(=2r) represents diameter of particles. In an embodiment, using Mie theory, the extinction efficiency $Q_{ext}$ is expressed as given in equation (4), $$Q_{ext} = \frac{2}{x^2} \sum_{n=1}^{\infty} (2n+1)\text{Re}(a_n + b_n) \tag{4}$$

Here, $a_n$ and $b_n$ are Mie coefficients which are function of m and x. m is expressed as, $m=n_p/n_m$, where $n_p$ and $n_m$ are the refractive indices of the particles and surrounding medium, respectively. Here, x is the size parameter and can be represented as $x=2\pi r n_m/\lambda$. where $\lambda$ is the wavelength. The scattering efficiency $Q_{sca}$ can be expressed as given in equation (5), $$Q_{sca} = \frac{2}{x^2} \sum_{n=1}^{\infty} (2n+1)\left(|a_n|^2 + |b_n|^2\right) \tag{5}$$

Since $Q_{ext}=Q_{sca}+Q_{abs}$, $Q_{abs}$ can be evaluated by subtracting $Q_{sca}$ from $Q_{ext}$. The numerical values of the Mie efficiency parameters are computed using the subroutine from Matzler's MATLAB functions. In an embodiment, Beer-Lambert law can be used to obtain the extinction coefficient ($\varepsilon$) of the nanoparticles from total absorbance as given in equation (6), $$A = \varepsilon l c \tag{6}$$

Therefore, using equation (3), extinction coefficient ($\varepsilon$) can be represented as given in equation (7), $$\varepsilon = \frac{Q_{ext}}{1.535 \rho d} \tag{7}$$

The SPF values have been estimated from the absorbance values by utilizing the following correlation given in equation (8), $$SPF_{Spectrophotometric} = CF \times \sum_{290}^{320} EE(\lambda) \times I(\lambda) \times \text{Abs}(\lambda) \tag{8}$$

where, $EE(\lambda)$ is the erythemal effect spectrum, $I(\lambda)$ is the solar intensity spectrum, $\text{Abs}(\lambda)$ is the absorbance and CF (=10) is the correction factor. The values of $EE(\lambda) \times I(\lambda)$ are constants.

In an embodiment, the equation (4) and equation (5) are used to calculate the relative extinction, scattering and absorption efficiency values while varying the diameter of chitosan nanoparticles. Since human skin exhibits maximum erythemal response when exposed to an irradiation wavelength of 310 nm, this particular wavelength is considered for all the calculations. Air, water and ethanol have been chosen as surrounding medium for dispersing the particles considering sunscreen in the form of powder, aqueous and alcoholic formulation, respectively.

Figure 1B:
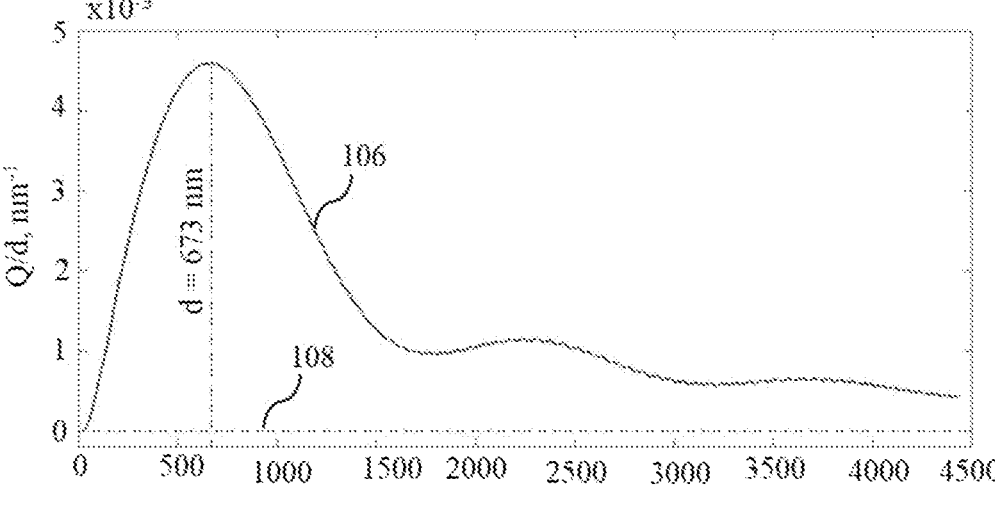
Figure 1C:
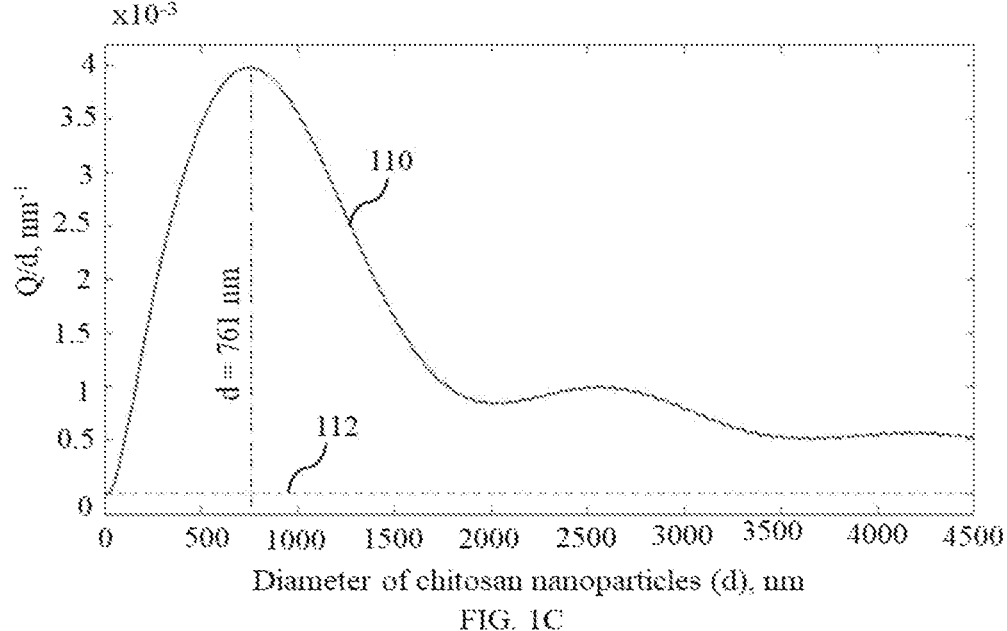

FIGS. 1A, 1B and 1C are graphs showing a relative extinction efficiency ($Q_{ext}/d$), a relative scattering efficiency ($Q_{sca}/d$), and a relative absorption efficiency ($Q_{abs}/d$) of the chitosan nanoparticles in air medium, water medium and ethanol medium respectively, in accordance with some embodiments of the present disclosure.

Now referring to FIGS. 1A, 1B and 1C, a complete overlap of the relative extinction efficiency values (the relative extinction efficiency plots are invisible in FIGS. 1A, 1B and 1C due to overlapping with scattering efficiency plots) with the scattering efficiency values is observed, indicating negligible contribution of absorption on the overall extinction by the chitosan nanoparticles in all the mediums. Now referring to FIG. 1A, the relative scattering efficiency in air medium is shown as 102 and the relative absorption efficiency in air medium is shown as 104. Now referring to FIG. 1B, the relative scattering efficiency in water medium is shown as 106 and the relative absorption efficiency in water medium is shown as 108. Now referring to FIG. 1C, the relative scattering efficiency in ethanol medium is shown as 110 and the relative absorption efficiency in ethanol medium is shown as 112. The maximum relative extinction efficiency values are observed when the size of chitosan nanoparticles is 268 nm (as shown in FIG.

1A), 673 nm (as shown in FIG. 1B) and 761 nm (as shown in FIG. 1C) in air, water, and ethanol medium, respectively. This means that the chitosan nanoparticles of the above standardized sizes will offer maximum attenuation of UV light having wavelength of 310 nm in the respective mediums.

Figure 2A:
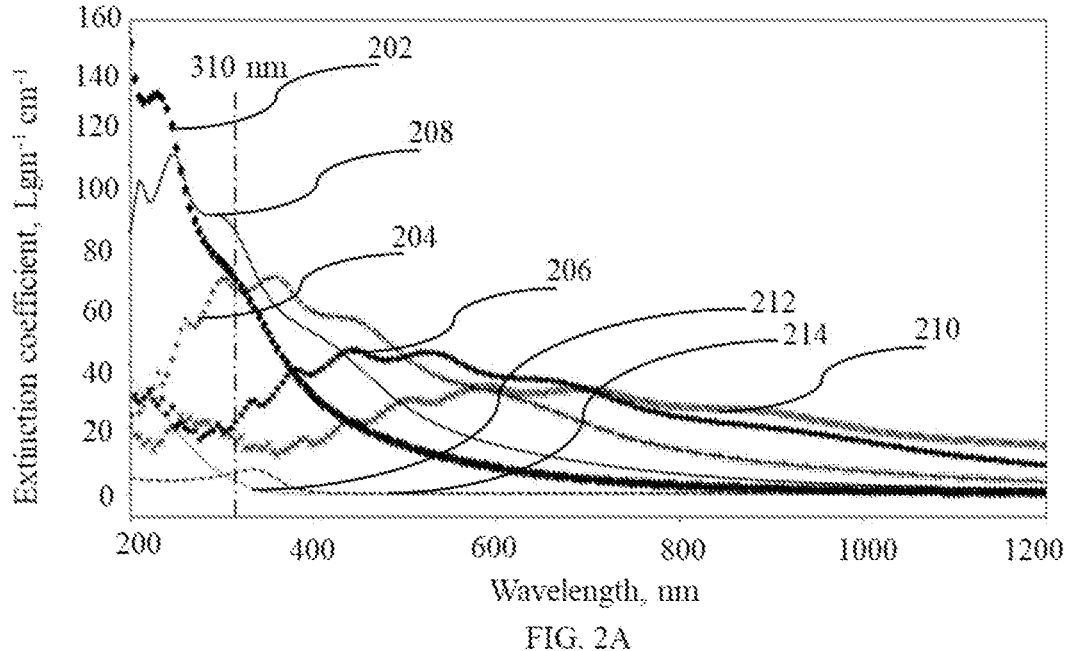
FIGS. 2A, 2B and 2C are graphs representing the extinction coefficient of chitosan nanoparticles of different sizes and commercial sunscreen nanoparticles of titania (size 15 nm) and zinc oxide (size 30 nm) at varying wavelength in air, water and ethanol medium, respectively, in accordance with some embodiments of the present disclosure.
Figure 2B:
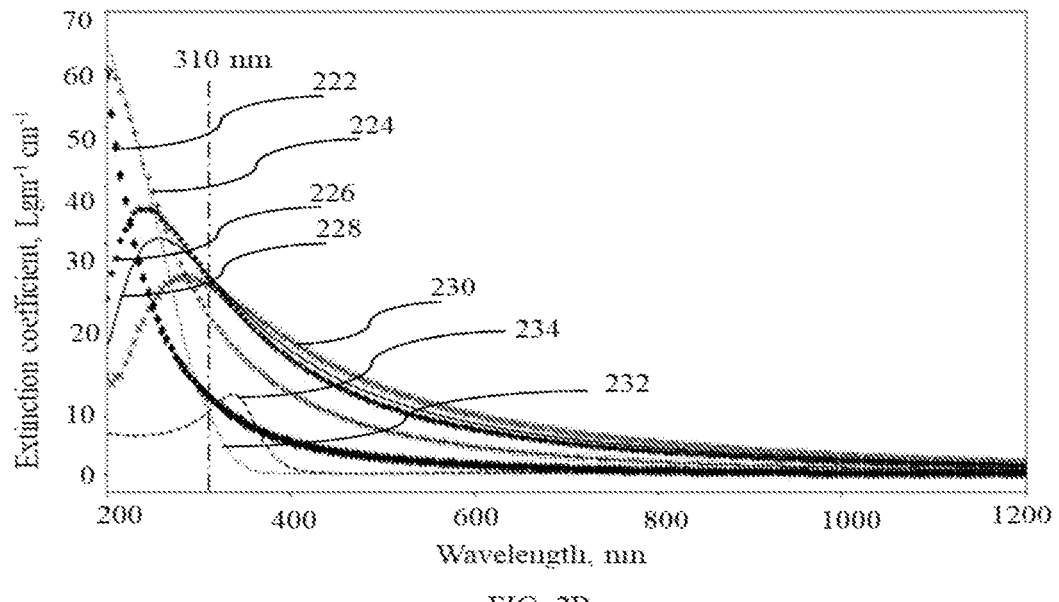
Figure 2C:
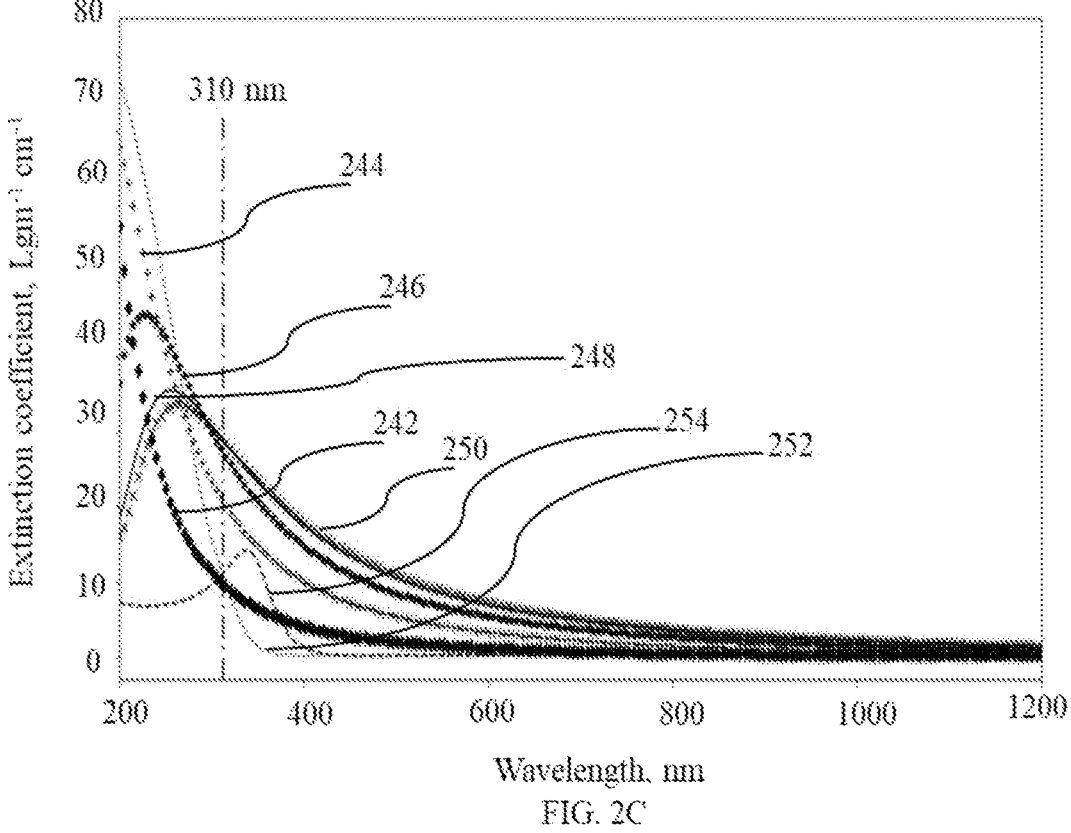

FIGS. 2A, 2B and 2C are graphs representing the extinction coefficient of chitosan nanoparticles of different sizes and commercial titania/zinc oxide sunscreen nanoparticles at varying wavelength in air, water and ethanol medium, respectively, in accordance with some embodiments of the present disclosure.

Now referring to FIG. 2A, the extinction coefficient values of chitosan nanoparticles of sizes 200 nm (shown in curve 202), 400 nm (shown in curve 204), 600 nm (shown in curve 206), 268 nm (shown in curve 208), 800 nm (shown in curve 210), titania nanoparticles of size 15 nm (shown in curve 212) and zinc oxide nanoparticles of size 30 nm (shown in curve 214) in air medium are compared.

Now referring to FIG. 2B, the extinction coefficient values of chitosan nanoparticles of sizes 200 nm (shown in curve 222), 400 nm (shown in curve 224), 600 nm (shown in curve 226), 673 nm (shown in curve 228), 800 nm (shown in curve 230), titania nanoparticles of size 15 nm (shown in curve 232) and zinc oxide nanoparticles of size 30 nm (shown in curve 234) in water medium are compared.

Now referring to FIG. 2C, the extinction coefficient values of chitosan nanoparticles of sizes 200 nm (shown in curve 242), 400 nm (shown in curve 244), 600 nm (shown in curve 246), 761 nm (shown in curve 248), 800 nm (shown in curve 250), titania nanoparticles of size 15 nm (shown in curve 252) and zinc oxide nanoparticles of size 30 nm (shown in curve 254) in ethanol medium are compared.

It can be seen from FIGS. 2A, 2B and 2C that chitosan nanoparticles of standardized sizes i.e., 268 nm, 673 nm and 761 nm exhibit maximum extinction coefficient at and around 310 nm wavelength (marked as a dotted line) in air, water and ethanol medium, respectively as compared to other sizes of chitosan nanoparticles and commercial sunscreen nanoparticles. Based on FIG. 2A, the chitosan nanoparticles of standardized size (curve 208) have an extinction co-efficient in the range of 40-100 $Lgm^{-1}cm^{-1}$ in air medium under UV radiation in the wavelength range of 290-400 nm. Based on FIG. 2B, the chitosan nanoparticles of standardized size (curve 228) have an extinction co-efficient in the range of 10-40 $Lgm^{-1}cm^{-1}$ in water medium under UV radiation in the wavelength range of 290-400 nm. Based on FIG. 2C, the chitosan nanoparticles of standardized size (curve 248) have an extinction co-efficient in the range of 10-30 $Lgm^{-1}cm^{-1}$ in ethanol medium under UV radiation in the wavelength range of 290-400 nm.

In an embodiment, the total absorbance (combining scattering and absorption) by chitosan nanoparticles is computed using the above extinction coefficient values and equation (6). The absorbance values of varied sizes of chitosan nanoparticles are compared with commercial titania and zinc oxide sunscreen nanoparticles. In an embodiment, the concentration (c) of all types of nanoparticles is considered to be 0.005 wt % and path length (1) to be 1 cm for calculating the absorbance values.

Figure 3A:
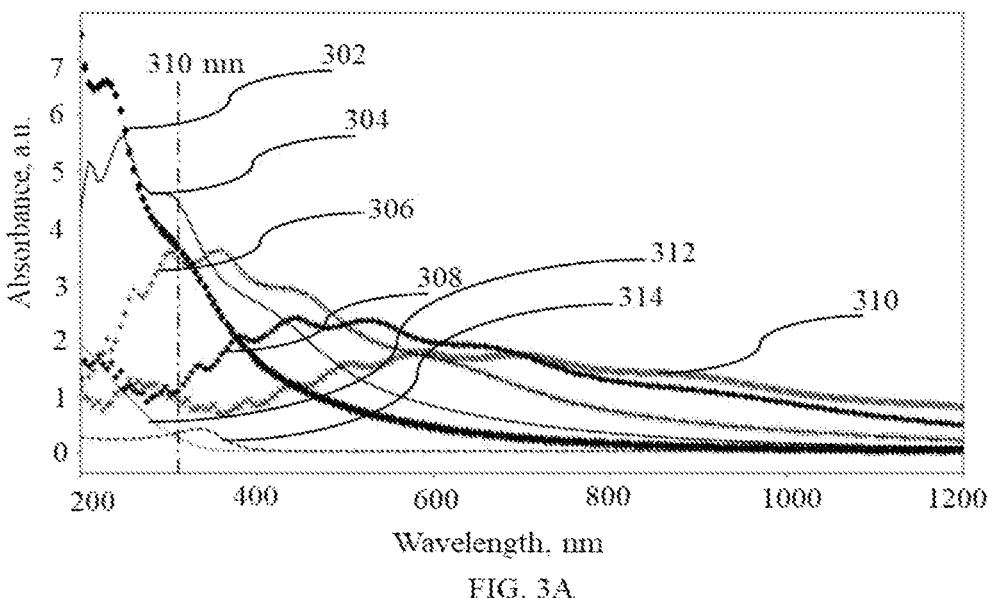
FIGS. 3A, 3B and 3C are graphs representing the total absorbance of chitosan nanoparticles of different sizes and commercial sunscreen nanoparticles of titania (size 15 nm) and zinc oxide (size 30 nm) at varying wavelength in air, water and ethanol medium, respectively, in accordance with some embodiments of the present disclosure.
Figure 3B:
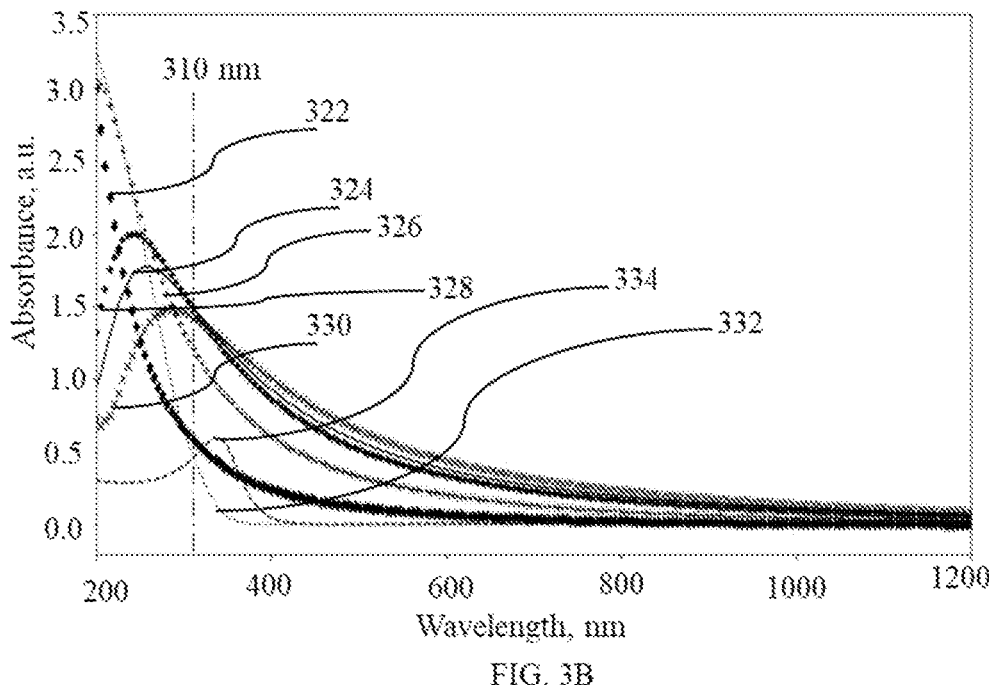
Figure 3C:
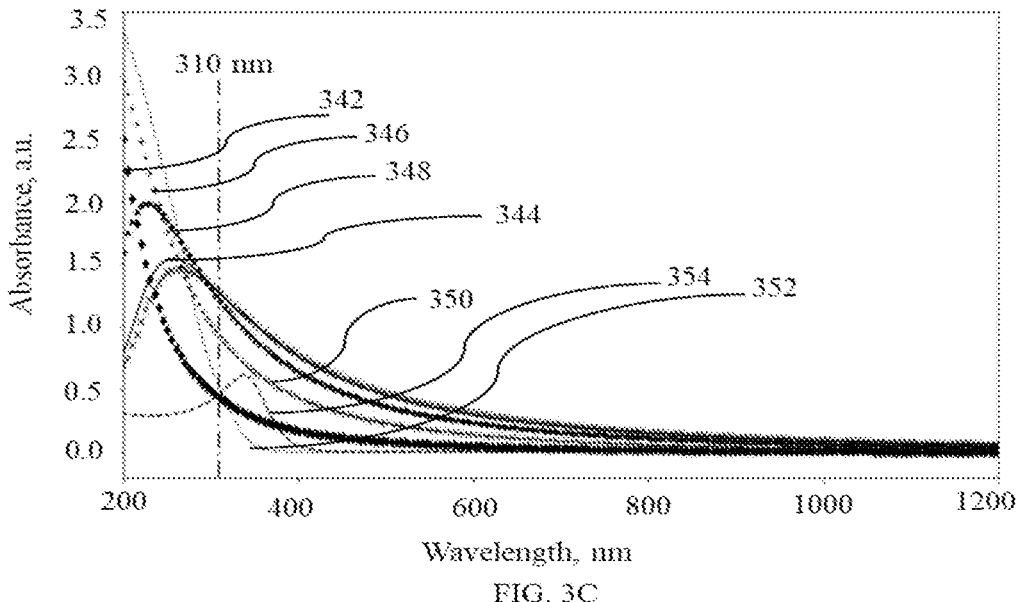

FIGS. 3A, 3B and 3C are graphs representing the total absorbance of chitosan nanoparticles of different sizes and commercial titania/zinc oxide sunscreen nanoparticles at varying wavelength in air, water and ethanol medium, respectively, in accordance with some embodiments of the present disclosure.

Now referring to FIG. 3A, the chitosan nanoparticles of sizes 200 nm (shown in curve 302), 268 nm (shown in curve 304), 400 nm (shown in curve 306), 600 nm (shown in curve 308), 800 nm (shown in curve 310), titania nanoparticles of size 15 nm (shown in curve 312) and zinc oxide nanoparticles of size 30 nm (shown in curve 314) in air medium are compared.

Now referring to FIG. 3B, the chitosan nanoparticles of sizes 200 nm (shown in curve 322), 673 nm (shown in curve 324), 400 nm (shown in curve 326), 600 nm (shown in curve 328), 800 nm (shown in curve 330), titania nanoparticles of size 15 nm (shown in curve 332) and zinc oxide nanoparticles of size 30 nm (shown in curve 334) in water medium are compared.

Now referring to FIG. 3C, the chitosan nanoparticles of sizes 200 nm (shown in curve 342), 761 nm (shown in curve 344), 400 nm (shown in curve 346), 600 nm (shown in curve 348), 800 nm (shown in curve 350), titania nanoparticles of size 15 nm (shown in curve 352) and zinc oxide nanoparticles of size 30 nm (shown in curve 354) in ethanol medium are compared.

As shown in FIGS. 3A, 3B and 3C, the standardized chitosan nanoparticles (size in air: 268 nm; size in water: 673 nm and size in ethanol: 761 nm) possess significantly higher absorbance values when irradiated by 310 nm wavelength in the corresponding mediums.

In an embodiment, SPF is considered to be a standard and traditionally recognized parameter for estimation of the efficacy of a sunscreen. SPF is defined as the ratio of the amount of UV irradiation required to cause sunburn on a sunscreen applied skin to that of a bare skin. Hence, higher SPF values of a sunscreen formulation correspond to higher amount of protection from harmful UV rays. The present disclosure has utilized equation (8) to measure the SPF values from the absorbance values of chitosan and commercial sunscreen nanoparticles. The standardized chitosan nanoparticles of sizes 268 nm, 673 nm and 761 nm exhibit highest SPF values in air, water and ethanol, respectively as compared to other chitosan nanoparticles and commercial $TiO_2$/ZnO nanoparticles which is consistent with the results obtained before. Overall, the results associated with the present disclosure suggest that chitosan nanoparticles of the above standardized sizes can provide better protection from UV irradiation than existing commercial sunscreen nanoparticles. Therefore, the proposed sunscreen comprising skin-adhering, biocompatible, biodegradable, antimicrobial chitosan nanoparticles will also possess superior UV attenuation capability than the existing sunscreen formulations.

Figure 4A:
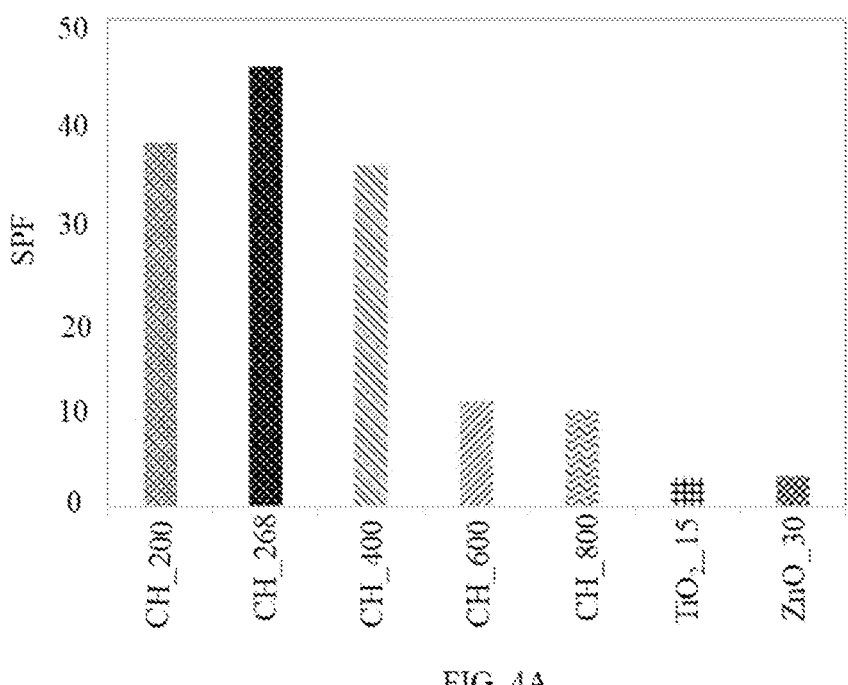
FIGS. 4A, 4B and 4C illustrates the SPF values exhibited by different sizes of chitosan nanoparticles (abbreviated as CH), commercial sunscreen nanoparticles of titania (size 15 nm) and zinc oxide (size 30 nm) in air, water and ethanol medium respectively, in accordance with some embodiments of the present disclosure.
Figure 4B:
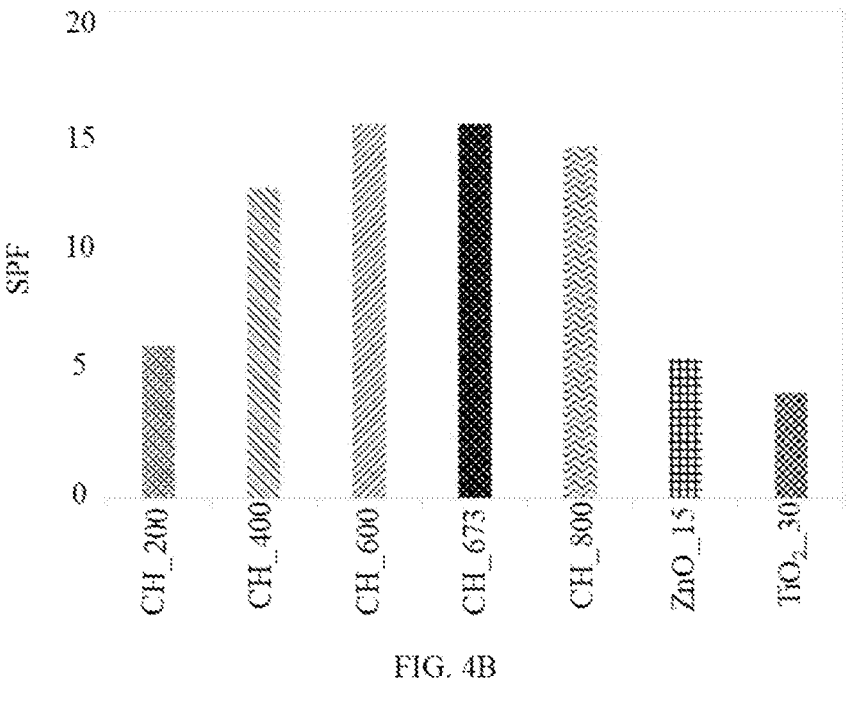
Figure 4C:
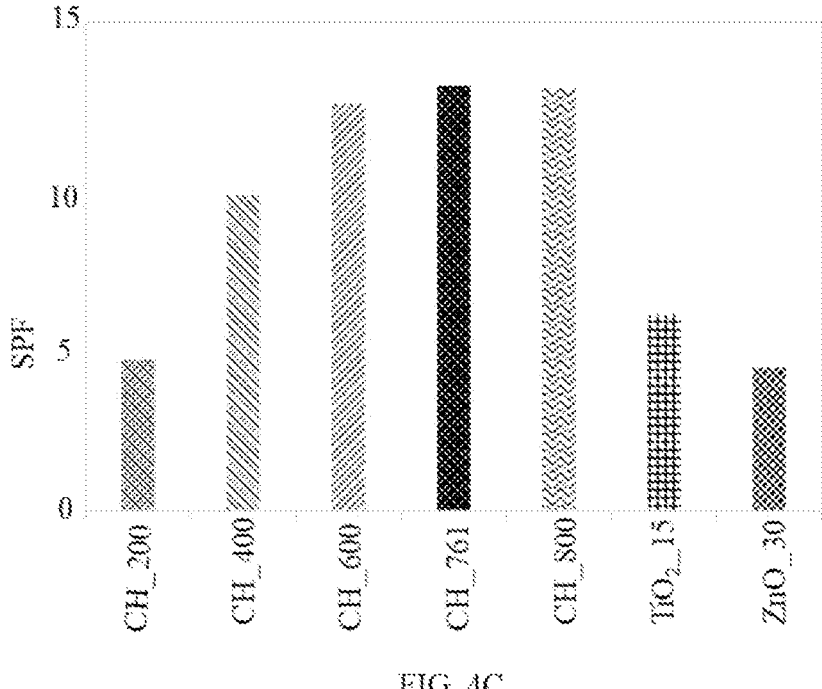

FIGS. 4A, 4B and 4C illustrate the SPF values exhibited by different sizes of chitosan nanoparticles (abbreviated as CH) and commercially available $TiO_2$ (size 15 nm) and ZnO (size 30 nm) sunscreen nanoparticles in air, water and ethanol medium respectively, in accordance with some embodiments of the present disclosure. Now referring to FIGS. 4A, 4B and 4C, the chitosan nanoparticles of size 268 nm in air medium, 600 nm and 673 nm in water medium and 761 nm and 800 nm in ethanol medium are providing high SPF values.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope of disclosed embodiments being indicated by the following claims.

What is claimed is:

1. A sunscreen composition comprising chitosan nanoparticles as UV filter, at least one flavoring agent, at least one coloring agent, at least one stabilizer, and at least one preservative, wherein the sunscreen composition is present in a defined form and size of the chitosan nanoparticles ranging from 200 to 900 nm, wherein the size of the chitosan nanoparticles ranging from 200 to 400 nm for air medium, 500 to 700 nm for water medium and 700 to 900 nm for ethanol medium, wherein the chitosan nanoparticles provide attenuation from ultraviolet (UV) radiation in a wavelength range of 290-400 nm.

2. The sunscreen composition as claimed in claim 1, wherein the chitosan nanoparticles comprise one of, a) a chitosan polymer and b) derivatives of chitosan polymer.

3. The sunscreen composition as claimed in claim 2, wherein the chitosan polymer is derived from chitin, wherein chitin is a glucosamine polymer.

4. The sunscreen composition as claimed in claim 2, wherein the chitosan polymer is non-toxic, biodegradable and biocompatible.

5. The sunscreen composition as claimed in claim 2, wherein the chitosan polymer is a cationic polymer.

6. The sunscreen composition as claimed in claim 1, wherein the chitosan nanoparticles provide antimicrobial protection of human skin from harmful pathogens owing to the antimicrobial property of chitosan polymer.

7. The sunscreen composition as claimed in claim 1, wherein the chitosan nanoparticles can adhere well on human skin owing to the cationic nature of chitosan polymer.

8. The sunscreen composition as claimed in claim 1, wherein the chitosan nanoparticles have an extinction co-efficient in the range of 40-100 $\text{Lgm}^{-1} \text{ cm}^{-1}$ in air medium under UV radiation in the wavelength range of 290-400 nm.

9. The sunscreen composition as claimed in claim 1, wherein the chitosan nanoparticles have an extinction co-efficient in the range of 10-40 $\text{Lgm}^{-1} \text{ cm}^{-1}$ in water medium under UV radiation in the wavelength range of 290-400 nm.

10. The sunscreen composition as claimed in claim 1, wherein the chitosan nanoparticles have an extinction co-efficient in the range of 10-30 $\text{Lgm}^{-1} \text{ cm}^{-1}$ in ethanol medium under UV radiation in the wavelength range of 290-400 nm.

11. The sunscreen composition as claimed in claim 1, wherein the defined form is selected from a group consisting of a skin cream, a skin lotion, a powder, a gel, and a sprayable liquid.

12. The sunscreen composition as claimed in claim 1, wherein the sunscreen composition is capable of protecting skin from harmful UV radiation.

13. The sunscreen composition as claimed in claim 1, wherein the size of the chitosan nanoparticles is determined using Mie theory.

* * * * *